United States Patent [19]

Sugimoto et al.

[11] Patent Number: 5,756,347
[45] Date of Patent: *May 26, 1998

[54] TEMPERATURE-SENSITIVE PLASMID

[75] Inventors: Masakazu Sugimoto; Hiroyuki Kojima; Akiko Tanaka; Hiroshi Matsui; Katsuaki Sato; Tsuyoshi Nakamatsu, all of Kawasaki, Japan

[73] Assignee: Ajinomoto Co., Inc., Tokyo, Japan

[*] Notice: The term of this patent shall not extend beyond the expiration date of Pat. No. 5,616,480.

[21] Appl. No.: 766,488

[22] Filed: Dec. 13, 1996

Related U.S. Application Data

[63] Continuation of Ser. No. 408,188, Mar. 22, 1995, Pat. No. 5,616,480, which is a continuation of Ser. No. 182,361, Jan. 18, 1994, which is a continuation of Ser. No. 774,846, Oct. 11, 1991.

Foreign Application Priority Data

Oct. 15, 1990 [JP] Japan ................................. 2-273348
Jun. 19, 1991 [JP] Japan ................................. 3-245291

[51] Int. Cl.$^6$ .......................... C12N 15/77; C12N 15/63; C12N 1/21
[52] U.S. Cl. ................................. 435/320.1; 435/252.32
[58] Field of Search ........................... 435/320.1, 252.32

[56] References Cited

U.S. PATENT DOCUMENTS 5,616,480  4/1997  Sugimoto et al. .............. 435/172.3

OTHER PUBLICATIONS

Sasakawa et al., Gene 56:283–288 (1987).
Serwold–Davis et al., FEMS Microbiology Letters 66:119–124 (1990).
Ito et al., Agric. Biol. Chem. 54:707–713 (1990).
Miller et al., Journal of Bacteriology 170(6):2575–2583 (1988).

Primary Examiner—Johnny F. Railey, II
Attorney, Agent, or Firm—Oblon, Spivak, McClelland, Maier & Neudstadt, P.C.

[57] ABSTRACT

A plasmid having a temperature-sensitive replication origin which has the following properties:

a) capable of autonomous replication in Corynebacterium and being retained in Corynebacterium; and, b) when a cell containing said plasmid is cultured at 31° to 37° C., replication of the plasmid is inhibited and at the same time, the plasmid is removed from the cell body; and a method for performing homologous recombination in Corynebacterium using the plasmid.

5 Claims, 2 Drawing Sheets

TEMPERATURE-SENSITIVE PLASMID

This is a Continuation of application Ser. No. 08/408,188 filed on Mar. 22, 1995, now U.S. Pat. No. 5,616,480; which is a Continuation of Ser. No. 08/182,361, filed on Jan. 18, 1994, abandoned; which is a continuation of Ser. No. 07/774,846, filed on Oct. 11, 1991, abandoned.

BACKGROUND OF THE INVENTION

1. Field of the Invention

The present invention relates to a method for modifying a chromosomal gene of Corynebacterium which is used for the production of useful substances such as amino acids by fermentation, resulting in a modification of its genetic character.

2. Discussion of the Background

Many attempts have been made to modify the genetic character of Corynebacterium by genetic engineering techniques and utilize the same for production of useful substances such as amino acids by fermentation. However, these methods all utilize a plasmid capable of autonomous replication as a vector (Japanese Patent Application Laid-Open Nos. 58-192900, 58-21699).

Plasmids replicate and function outside the chromosome. Therefore, where the genetic character of a bacterium is modified using plasmid DNA, the modification cannot be extended to the chromosome of the host bacterium. In particular, where DNA properties of the host bacterium, such as deletion, mutation, etc. come at issue, it has been impossible to make purposeful changes. To date, there is a method which comprises treating a host bacterium with a mutagen and then selecting a strain modified at random which has the desired properties, but this method involves much labor and many difficulties. Also, where plasmid DNA is used, the plasmid is often unstable and is expelled from the cell so that sufficient expression cannot be obtained or, many copies of the plasmid bearing the desired gene are present, whereby expression becomes excessive and such adversely affects the growth of bacteria or production of a substance. An object of the present invention is to modify a specific gene on the chromosome along the plan and fixing a definite number of copies of the gene stably on the chromosome, thereby to solve these problems.

SUMMARY OF THE INVENTION

An object of the invention is to provide a method whereby the replication origin of plasmid DNA capable of autonomous replication in Corynebacterium is converted into being incapable of autonomous replication by elevating the culture temperature, whereby there can be obtained the effects that a specific gene on the chromosome can be intentionally modified and a definite copy number of the gene can be stably fixed on the chromosome.

DETAILED DESCRIPTION OF THE PREFERRED EMBODIMENTS

As a result of extensive investigations to solve the foregoing problems, the present inventors have succeeded in modifying the replication origin of plasmid DNA capable of autonomous replication in Corynebacterium to the replication origin of temperature-sensitive mutant type which cannot replicate at a high temperature.

The desired gene is ligated with a plasmid having this temperature-sensitive replication origin and a strain in which the plasmid has been borne is cultured firstly at 10° to 27° C., preferably at 20° to 25° C. and then at 31° to 37° C., preferably at 33° to 36° C. to remove the plasmid. A strain having the gene integrated in the chromosome is selected. In this case, a marker gene such as a drug-resistant gene on the plasmid is integrated into the chromosome. Though the plasmid is not borne, the integrated strain shows the character of the marker gene such as drug resistance and can be selected by detecting it.

At this stage, vector plasmid DNA and the desired gene are both integrated into the chromosome. However, using removal of the character of the marker gene as an index, the strains which have lost the vector portion from the chromosome due to homologous recombination again can be selected. In this case, gene replacement, in which the chromosomal gene of the host corresponding to the desired gene is concurrently removed and replaced by the gene infected with the plasmid, can be accomplished.

For integrating a gene into the chromosome, there is a method, in addition to the method described above, which comprises transfecting DNA incapable of replication and selecting a strain which has caused recombination. However, the present method using a temperature-sensitive plasmid can duplicate the desired gene intracellularly in a plasmid state and the plasmid-bearing strain can be duplicated, providing recombination with much higher frequency than the method for causing recombination by transfection of DNA incapable of replication. Therefore, the present invention is characterized in that the frequency of the recombinants that appear is hardly affected by the frequency of transformation of the host or by degradation of infected DNA, so that the method is highly generalized.

Examples of wild strains of Coryneform glutamic acid-producing bacteria include the following, but any other can be utilized as the host if the temperature-sensitive replication origin constructed herein functions in the bacteria and the plasmid is capable of replication.

*Brevibacterium divaricatum* ATCC 14020
*Brevibacterium saccharolyticum* ATCC 14066
*Brevibacterium immariophilum* ATCC 14068
*Brevibacterium lactofermentum* ATCC 13869
*Brevibacterium roseum* ATCC 13825
*Brevibacterium flavum* ATCC 13826
*Brevibacterium thiogenitalis* ATCC 19240
*Corynebacterium acetoacidophilum* ATCC 13870

*Corynebacterium acetoglutamicum* ATCC 15806

*Corynebacterium callunae* ATCC 15991

*Corynebacterium glutamicum* ATCC 13032, 13060

*Corynebacterium lilium* ATCC 15990

*Corynebacterium melassecola* ATCC 17965

*Microbacterium ammoniaphilum* ATCC 15354

Having generally described this invention, a further understanding can be obtained by reference to certain specific examples which are provided herein for purposes of illustration only and are not intended to be limiting unless otherwise specified.

EXAMPLE 1

Collection of temperature-sensitive replication origin and construction of plasmid vector for chromosomal integration. Construction of pHK4:

Firstly, as a material for collecting the temperature-sensitive replication origin, plasmid vector pHK4 which was capable of autonomous replication in cells of both *Escherichia coli* and Corynebacterium was prepared. Some reports were made on plasmid vectors which are capable of autonomous replication in cells of both *Escherichia coli* and Corynebacterium. Herein, novel shuttle vector pHK4 was constructed from pAJ1844 (cf. Japanese Patent Application-Laid Open No. 58-216199) and pHSG298 (cf., S. Takeshita et al: *Gene*, 61, 63–74 (1987)). pAJ1844 was partially digested with restriction enzyme Sau3AI and ligated with pHSG298 fully digested with restriction enzyme BamHI. *Brevibacterium lactofermentum* AJ12036 (FERM-P 7559) was transformed with the DNA after ligation. Transformation was performed according to the electroporation technique (cf. Japanese Patent Application Laid Open No. 2-207791). Selection of the transformants was made using M-CM2G plate (containing 5 g of glucose, 10 g of polypeptone, 10 g of yeast extract, 15 g of NaCl, 0.2 g of DL-methionine and 15 g of agar in 1 liter of pure water, pH 7.2) containing 25 µg/ml of kanamycin. Plasmid DNA was prepared from the transformants. The plasmid having the smallest size was selected and named pHK4. This plasmid is capable of autonomous replication in *Escherichia coli* and Corynebacterium and imparts kanamycin resistance to the host.

Figure 1:
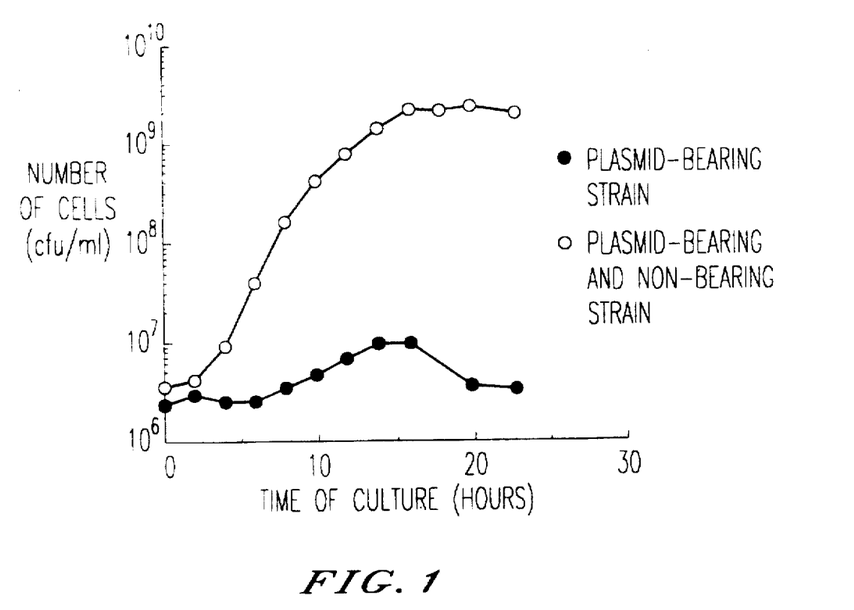
FIG. 1 shows the change in the plasmid retention property of AJ12036 strain bearing plasmid pHSC4 having a replication origin temperature-sensitive mutant type, when cultured at high temperature (34° C.). The plasmid retention property was determined by diluting liquid culture, spreading the dilution onto M-CM2G plate containing chloramphenicol and M-CM2G plate containing no drug, culturing at low temperature (20° C.), counting the numbers of both the colonies bearing plasmid and the colonies formed on M-CM2G plate without drug, and comparing them.
Figure 2:
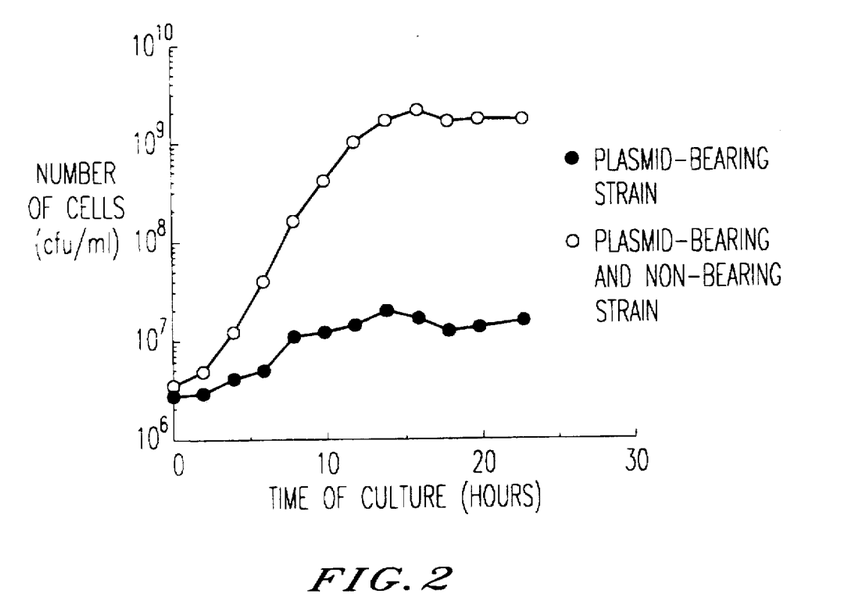
FIG. 2 shows the change in the plasmid retention property of pHSC22, as described above.
Figure 3:
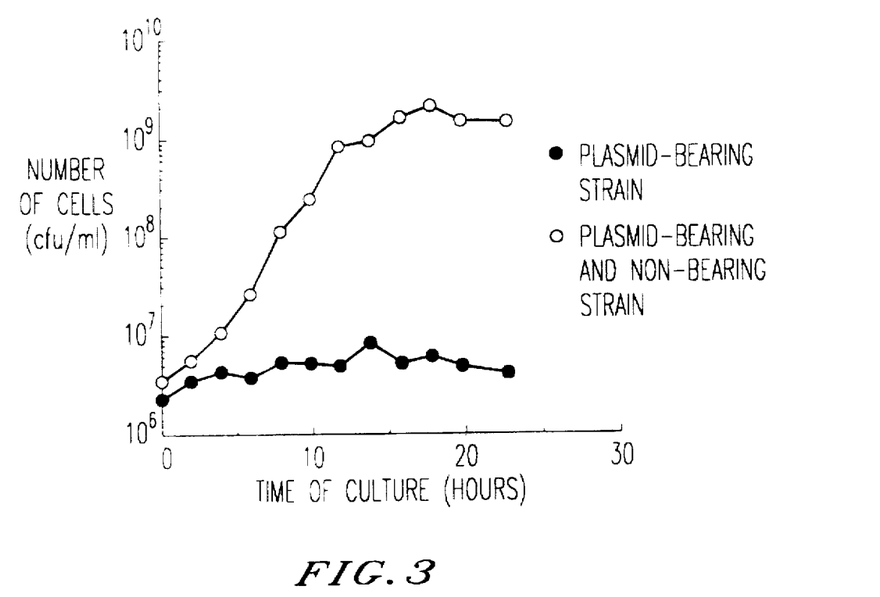
FIG. 3 shows the change in the plasmid retention property of pHSC23, as described above. The three plasmids above are those having a temperature-sensitive replication origin.
Figure 4:
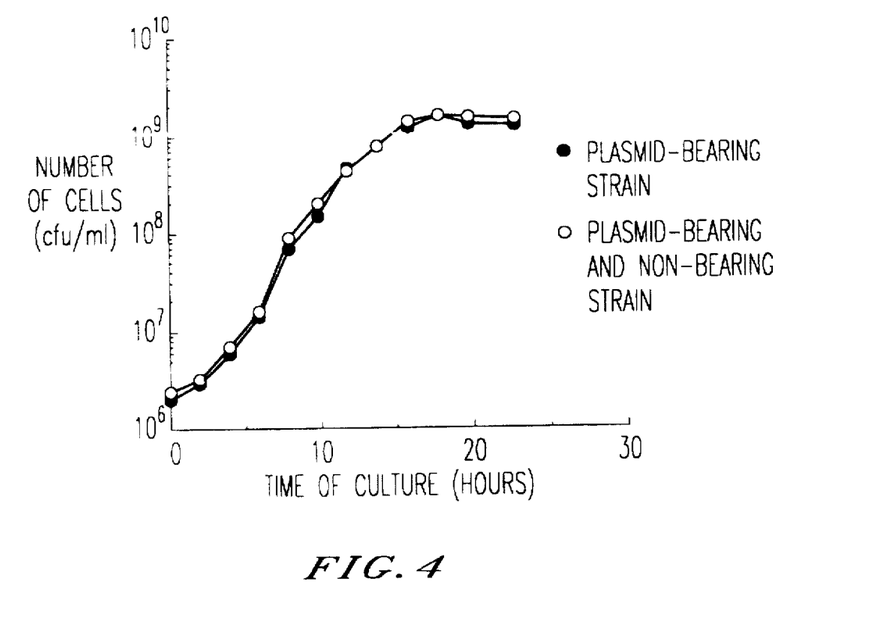
FIG. 4 shows the change in the plasmid retention property of AJ12036 strain bearing pHC4 (plasmid having a replication origin of wild type), as described above.

Collection of temperature-sensitive replication origin and construction of plasmid vector for chromosomal integration:

pHK4 was treated with hydroxylamine in vitro. The hydroxylamine treatment was carried out by a known method (G. O. Humpherys et al: *Molec. Gen. Genet.*, 145, 101–108 (1976)). After the treatment, DNA was recovered and *Brevibacterium lactofermentum* AJ12036 strain was transformed with it. The transformants were selected at low temperature (20° C.) on M-CM2G plate containing 25 µg/ml of kanamycin. The transformants that appeared were replicated onto a new plate of the same content and cultured at high temperature (34° C.). Three transformants which could not grow at the high temperature on the selective plate containing kanamycin were obtained. From the transformants, plasmids were recovered and named pHS4, pHS22 and pHS23. From *Escherichia coli* AJ12570 (FERM BP-3523) bearing pHS4 as the plasmid and *Escherichia coli* bearing each of pHS22 and pHS23, the plasmids were recovered. The DNA fragment derived from pAJ1844, which is the replication origin in Corynebacterium, was excised with restriction enzymes BamHI and KpnI and ligated with pHSG398 (cf., S. Takeshita et al: *Gene*, 61, 63–74, (1987)) which is a vector for *Escherichia coli*. These plasmids having replication origins derived from pHS4, pHS22 and pHS23 were named pHSC4, pHSC22 and pHSC23, respectively. In a similar manner, the replication origin in Corynebacterium from pHK4 was transferred to pHSG398 to prepare pHC4.

pHC4, pHSC4, pHSC22 and pHSC23 are capable of autonomous replication in Corynebacterium and *Escherichia coli* and impart chloramphenicol resistance to the host. It is also confirmed that the replication origins of pHSC4, pHSC22 and pHSC23 functioning in Corynebacterium are of temperature-sensitive type. From *Escherichia coli* AJ12571 (FERM BP-3524) bearing pHSC4 as plasmid, *Escherichia coli* AJ12615 (FERM BP-3530) bearing *Escherichia coli* pHSC22 as plasmid, *Escherichia coli* AJ12616 (FERM BP-3531) bearing pHSC23 as plasmid, and *Escherichia coli* AJ12617 (FERM BP-3532) bearing pHC4 as plasmid, the plasmids were prepared and transfected to *Brevibacterium lactofermentum* AJ12036. Change in retention ability of the plasmids was observed by culturing at high temperature (34° C.) in non-selective medium. Replication of pHSC4, pHSC22 and pHSC23 in AJ12036 was almost completely inhibited by the culture at high temperature (FIGS. 1, 2, 3 and 4).

Determination of the nucleotide sequence of temperature-sensitive replication origins:

Nucleotide sequences of the replication origin portions which function in Corynebacterium, of plasmid pHC4 having a replication origin of wild type, and plasmids pHSC4, pHSC22 and pHSC23 having replication origins of temperature-sensitive type were determined. The method for determining the nucleotide sequence was the method of Sanger et al (F. Sanger et al: *Proc. Natl. Acad. Sci.*, 74, 5463 (1977)). As the result, it was revealed that there was substitution of 2 to 4 nucleotides between the replication origin of wild type and the replication origins of temperature-sensitive mutant types. The nucleotide sequence of the temperature-sensitive replication origin region contained in pHSC4 and functioning in Corynebacterium is shown in Sequence ID NO: 1. The nucleotide sequence of the temperature-sensitive replication origin region contained in pHSC22 and functioning in Corynebacterium is shown in Sequence ID NO: 2. The nucleotide sequence of the temperature-sensitive replication origin region contained in pHSC23 and functioning in Corynebacterium is shown in Sequence ID NO: 3 and the nucleotide sequence of the wild type replication origin region contained in pHC4 and functioning in Corynebacterium is shown in Sequence ID NO: 4.

The mutation sites of the temperature-sensitive replication origin portions are as follows. With respect to pHSC4, 1543 G is mutated to A and 1546 G is mutated to A, on the sequence. With respect to pHSC22, 683 C is mutated to T, 1172 C is mutated to T, and 1615 C is mutated to T, on the sequence. With respect to pHSC23, 756 G is mutated to A, 1561 G is mutated to A, 1668 C is mutated to T and 1685 C is mutated to T, on the sequence.

EXAMPLE 2

Integration of DNA on plasmid into *Brevibacterium lactofermentum* chromosomal gene using plasmid vector for chromosomal integration.

It is known that 3-deoxy-D-arabinoheptulosonate-7-phosphate synthase gene (hereinafter abbreviated as "DS gene") in which feedback inhibition by tyrosine and phenylalanine has been substantially released imparts both resistance against m-fluorophenylalanine, which is analogous to phenylalanine, and productivity of phenylalanine and tyrosine to the strain of *Brevibacterium lactofermentum* (cf., Japanese Patent Application Laid-Open No. 61-124375). Using this property as an index, the DS gene was integrated into the chromosome of *Brevibacterium lactofermentum* wild strain by homologous recombination.
Preparation of plasmid for chromosomal integration:

After pAR-1, which is the plasmid bearing the DS gene in which feedback inhibition by tyrosine and phenylalanine has been substantially released (cf., Japanese Patent Application Laid-Open No. 61-124375) was partially digested with Sau3AI, the digestion product was ligated with pHK4 fully digested with restriction enzyme BamHI. The ligation product was transfected to *Brevibacterium lactofermentum* AJ12036 strain by electroporation.

The transformants were selected on minimum medium plate (containing 20 g of glucose, 5 g of $(NH_4)_2SO_4$, 2 g of urea, 1 g of $KH_2PO_4$, 5 g of $MgSO_4 \cdot 7H_2O$, 10 mg of $FeSO_4 \cdot 7H_2O$, 10 Mg of $MnSO_4 \cdot 4H_2O$, 50 μg of biotin, 2000 μg of thiamine hydrochloride and 15 g of agar in 1 liter of water, pH 6.6) containing 500 μg/ml of m-fluorophenylalanine. Plasmids were prepared from the transformants and the plasmid having the smallest size was selected. The plasmid was digested with restriction enzymes BamHI and SalI to recover a 1.9 kilobase fragment containing the DS gene. The fragment was ligated with pHSC4 digested with BamHI and SalI. The prepared plasmid was named pHSC4D.

Transfection of plasmid for integration into *Brevibacterium lactofermentum* and selection of the strain integration into chromosome:

Plasmid pHSC4D was prepared from *Escherichia coli* AJ12572 (FERM BP-3525) containing pHSC4D as plasmid and transfected to *Brevibacterium lactofermentum* AJ12036 strain by electroporation. The transformants were selected at 20° C. on M-CM2G plate containing 5 μg/ml of chloramphenicol. After the transfection, the obtained strain was cultured in M-CM2G plate medium. Thereafter, the culture broth was diluted into $10^3$ to $10^6$ cfu and the dilution was applied to M-CM2G plate containing 5 μg/ml of chloramphenicol. The plate was cultured at 34° C. The strain bearing the temperature-sensitive plasmid became sensitive to chloramphenicol since replication of the plasmid was inhibited at this temperature, so that no colony could be formed. However, since the strain having plasmid DNA integrated in the chromosome is resistant to chloramphenicol and forms colonies, it could be selected. It was confirmed by Southern hybridization and resistance of the integrated bacteria to m-fluorophenylalanine that the DS gene of mutant type derived from the plasmid vector had been integrated around the DS gene of the host chromosome by homologous recombination.

EXAMPLE 3

Collection of gene-replaced strain from the chromosome-integrated strain:

Firstly, chloramphenicol-sensitive strains were collected from AJ12573 strain (FERM BP-3526) having the DS gene integrated in the chromosome by homologous recombination. The integrated strains were diluted and the dilution was applied to M-CM2G plate followed by culturing at 34° C. After colony formation, replication was performed on M-CM2G plate containing 5 μg/ml of chloramphenicol followed by culturing at 34° C. The strains which became sensitive to chloramphenicol were collected.

From the strains which became sensitive to chloramphenicol, the strain which was sensitive to chloramphenicol and resistant to m-fluorophenylalanine was selected. Chloramphenicol sensitivity means that the plasmid vector has fallen off the chromosome by recombination and the m-fluorophenylalanine resistance means that DS gene of mutant type transfected from the plasmid still remains on the chromosome. In other words, upon the falling off of the gene from the chromosome by homologous recombination, the gene of mutant type transfected from the plasmid still remains associated with the chromosome, and the gene of wild type inherently present on the chromosome has recombined with the plasmid vector and disociated with the vector from the chromosome, thus causing gene replacement.

EXAMPLE 4

Production of tyrosine and phenylalanine by the mutant DS gene-integrated strain into the chromosome:

Tyrosine and phenylalanine were produced using AJ12573 strain (FERM BP-3526) in which the DS gene of mutant type had been integrated into the chromosome using the temperature-sensitive vector, and AJ12574 strain (FERM BP-3527) having the DS gene of mutant type fixed on the chromosome by gene replacement. After each strain was refreshed with M-CM2G plate, the strain was inoculated on phenylalanine productive medium (130 g of glucose, 10 g of $(NH_4)_2SO_4$, 1 g of $KH_2PO_4$, 1 g of $MgSO_4 \cdot 7H_2O$, 12 g of fumaric acid, 3 ml of acetic acid, 50 ml of soybean acid hydrolysate "AJI-EKI", 10 mg of $FeSO_4 \cdot 7H_2O$, 10 mg of $MnSO_4 \cdot 4H_2O$, 50 μg of biotin, 2000 μg of thiamine hydrochloride and 50 g of $CaCO_3$ in 1 liter of water, pH 7.0) followed by culturing at 31.5° C. for 48 hours. Amounts of tyrosine and phenylalanine in the culture broth after culture are as shown in Table 1.

TABLE 1

| Strain | AJ12036 | AJ12573 | AJ12574 |
|---|---|---|---|
| Amount of Tyr Production | 0.37 | 2.02 | 2.73 |
| Amount of Phe Production | 0 | 3.46 | 2.07 |

EXAMPLE 5

Integration of aspartate kinase gene of the feedback inhibition release-type into the chromosome of *Brevibacterium lactofermentum* wild strain and production of lysine using the integrated strain.

Preparation of the plasmid for gene integration:

Aspartokinase gene (hereinafter referred to as the "AK gene") in which feedback inhibition by lysine and threonine has been substantially released was obtained from *Corynebacterium glutamicum* lysine-producing bacteria AJ3463 (FERM-P 1987) as follows. Chromosomal DNA of AJ3463 was partially digested with restriction enzyme Sau3AI and the digestion product was ligated with pHSC4 completely digested with BamHI. This DNA was transformed to AJ12036 strain. The transformants were selected at 20° C. in minimum medium containing 5 μg/ml of chloramphenicol, 100 mg/dl of L-threonine and 3000 μg/ml of S-(2-aminoethyl)-L-cystein (hereinafter referred to as "AEC"). From the transformant, a plasmid was prepared and named pHSC4AE.

Integration of inhibition release type AK gene into *Brevibacterium lactofermentum* chromosome and collection of the gene-replaced strain:

*Brevibacterium lactofermentum* ATCC13869 strain was transformed by plasmid pHSC4AE. The transformant was selected at 20° C. The transformant was diluted in sterile water in $10^3$ to $10^5$ cfu per plate and the dilution was spread on M-CM2G plate. After culturing 34° C., the strains which formed colonies were selected as the gene-integrated strains. From the gene-integrated strains, the chloramphenicol-sensitive strains were again obtained and a strain which was sensitive to chloramphenicol and resistant to AEC was selected as the gene-replaced strain.

Production of lysine using the gene-replaced strain:

*Brevibacterium lactofermentum* AJ12575 strain (FERM BP-3528) having inhibition release-type AK gene integrated into the chromosome by gene replacement, and its parent strain ATCC13869, were inoculated on lysine productive medium (100 g of glucose, 55 g of $(NH_4)_2SO_4$, 1 g of $KH_2PO_4$, 1 g of $MgSO_4 \cdot 7H_2O$, 50 ml of soybean acid hydrolysate "MAMENO", 10 mg of $FeSO_4 \cdot 7H_2O$, 10 mg of $MnSO_4 \cdot 4H_2O$, 5 mg of nicotinamide, and 50 g of $CaCO_3$ in 1 liter of water, pH 8.0) followed by culturing at 31.5° C. for 48 hours. The amount of lysine in the culture broth after culture is shown in Table 2.

TABLE 2

| Strain | ATCC13869 | AJ12575 |
|---|---|---|
| Amount of Lys Production | 0.1 | 17.5 |

Having now fully described the invention, it will be apparent to one of ordinary skill in the art that many changes and modifications can be made thereto without departing from the spirit or scope of the invention as set forth herein.

What is claimed is:

1. A plasmid having a temperature-sensitive replication origin derived from plasmid pHSC4, pHSC22 or pHSC23.
2. The plasmid of claim 1 comprising Sequence ID No: 1.
3. The plasmid of claim 1 comprising Sequence ID No: 2.
4. The plasmid of claim 1 comprising Sequence ID No: 3.
5. The plasmid of claim 1 comprising a DNA sequence analogous to a genetic sequence present on the chromosome of Corynebacterium encoding 3-deoxy-D-arabinoheptulosonate-7-phosphate synthase derived from *Brevibacterium lactofermentum* in which feedback inhibition by tyrosine and phenylalanine has been released.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2959 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Corynebacterium glutamicum
        ( B ) STRAIN: ATCC 13058

( x i ) SEQUENCE DESCRIPTION: SEQ ID NO:1:

```
GGATCCGGTG TATGCCGCAG CAGGCATGAG CAGCCCGAAT ATGCGCCTGC TGGCTGCAAC        60
GACCGAGGAA ATGACCCGCG TTTTCGGCGC TGACCAGGCT TTTTCACATA GGCTGAGCCG       120
GTGGCCACTG CACGTCTCCG ACGATCCCAC CGCGTACCGC TGGCATGCCC AGCACAATCG       180
CGTGGATCGC CTAGCTGATC CCGAAAAAGT TTTTGCCTTT TGTAAAAAAC TTCTCGGTCG       240
CCCCGCAAAT TTCGATTCC AGATTTTTTA AAAACCAAGC CAGAAATACG ACACACCGTT        300
TGCAGATAAT CTGTCTTTCG GAAAAATCAA GTGCGATACA AAATTTTTAG CACCCCTGAC       360
GTGCGCAAAG TCCCGCTTCG TGAAAATTTT CGTGCCGCGT GATTTTCCGC CAAAAACTTT       420
AACGAACGTT CGTTATAATG GTGTCATGAC CTTCACGACG AAGTACCAAA ATTGGCCCGA       480
ATCATCAGCT ATGGATCTCT CTGATGTCGC GCTGGAGTCC GACGCGCTCG ATGCTGCCGT       540
CGATTTAAAA ACGGTGATCG GATTTTTCCG AGCTCTCGAT ACGACGGACG CGCCAGCATC       600
ACGAGACTGG GCCAGTGCCG CGAGCGACCT AGAAACTCTC GTGGCGGATC TTGAGGAGCT       660
GGCTGACGAG CTGCGTGCTC GGCAGCGCCA GGAGGACGCA CAGTAGTGGA GGATCGAATC       720
AGTTGCGCCT ACTGCGGTGG CCTGATTCCT CCCCGGCCTG ACCCGCGAGG ACGGCGCGCA       780
AAATATTGCT CAGATGCGTG TCGTGCCGCA GCCAGCCGCG AGCGCGCCAA CAAACGCCAC       840
GCCGAGGAGC TGGAGGCGGC TAGGTCGCAA ATGGCGCTGG AAGTGCGTCC CCCGAGCGAA       900
ATTTTGGCCA TGGTCGTCAC AGAGCTGGAA GCGGCAGCGA GAATTATCCG CGATCGTGGC       960
GCGGTGCCCG CAGGCATGAC AAACATCGTA AATGCCGCGT TTCGTGTGGC CGTGGCCGCC      1020
CAGGACGTGT CAGCGCCGCC ACCACCTGCA CCGAATCGGC AGCAGCGTCG CGCGTCGAAA      1080
AAGCGCACAG GCGGCAAGAA GCGATAAGCT GCACGAATAC CTGAAAAATG TTGAACGCCC      1140
CGTGAGCGGT AACTCACAGG GCGTCGGCTA ACCCCCAGTC CAAACCTGGG AGAAAGCGCT      1200
```

```
CAAAAATGAC TCTAGCGGAT TCACGAGACA TTGACACACC GGCCTGGAAA TTTTCCGCTG    1260
ATCTGTTCGA CACCCATCCC GAGCTCGCGC TGCGATCACG TGGCTGGACG AGCGAAGACC    1320
GCCGCGAATT CCTCGCTCAC CTGGGCAGAG AAAATTTCCA GGGCAGCAAG ACCCGCGACT    1380
TCGCCAGCGC TTGGATCAAA GACCCGGACA CGGGAGAAAC ACAGCCGAAG TTATACCGAG    1440
TTGGTTCAAA ATCGCTTGCC CGGTGCCAGT ATGTTGCTCT GACGCACGCG CAGCACGCAG    1500
CCGTGCTTGT CCTGGACATT GATGTGCCGA GCCACCAGGC CAGCAGGAAA ATCGAGCACG    1560
TAAACCCCGA GGTCTACGCG ATTTTGGAGC GCTGGGCACG CCTGGAAAAA GCGCCAGCTT    1620
GGATCGGCGT GAATCCACTG AGCGGGAAAT GCCAGCTCAT CTGGCTCATT GATCCGGTGT    1680
ATGCCGCAGC AGGCATGAGC AGCCCGAATA TGCGCCTGCT GGCTGCAACG ACCGAGGAAA    1740
TGACCCGCGT TTCGGCGCT GACCAGGCTT TTCACATAG GCTGAGCCGG TGCCACTGC       1800
ACGTCTCCGA CGATCCCACC GCGTACCGCT GGCATGCCCA GCACAATCGC GTGGATCGCC    1860
TAGCTGATCT TATGGAGGTT GCTCGCATGA TCTCAGGCAC AGAAAAACCT AAAAAACGCT    1920
ATGAGCAGGA GTTTCTAGC GGACGGGCAC GTATCGAAGC GGCAAGAAAA GCCACTGCGG     1980
AAGCAAAAGC ACTTGCCACG CTTGAAGCAA GCCTGCCGAG CGCCGCTGAA GCGTCTGGAG    2040
AGCTGATCGA CGGCGTCCGT GTCCTCTGGA CTGCTCCAGG GCGTGCCGCC CGTGATGAGA    2100
CGGCTTTTCG CCACGCTTTG ACTGTGGGAT ACCAGTTAAA AGCGGCTGGT GAGCGCCTAA    2160
AAGACACCAA GATCATCGAC GCCTACGAGC GTGCCTACAC CGTCGCTCAG GCGGTCGGAG    2220
CAGACGGCCG TGAGCCTGAT CTGCCGCCGA TGCGTGACCG CCAGACGATG GCGCGACGTG    2280
TGCGCGGCTA CGTCGCTAAA GGCCAGCCAG TCGTCCCTGC TCGTCAGACA GAGACGCAGA    2340
GCAGCCGAGG GCGAAAAGCT CTGGCCACTA TGGGAAGACG TGGCGGTAAA AAGGCCGCAG    2400
AACGCTGGAA AGACCCAAAC AGTGAGTACG CCCGAGCACA GCGAGAAAAA CTAGCTAAGT    2460
CCAGTCAACG ACAAGCTAGG AAAGCTAAAG GAAATCGCTT GACCATTGCA GGTTGGTTTA    2520
TGACTGTTGA GGGAGAGACT GGCTCGTGGC CGACAATCAA TGAAGCTATG TCTGAATTTA    2580
GCGTGTCACG TCAGACCGTG AATAGAGCAC TTAAGTCTGC GGGCATTGAA CTTCCACGAG    2640
GACGCCGTAA AGCTTCCAG TAAATGTGCC ATCTCGTAGG CAGAAACGG TTCCCCCGT       2700
AGGGGTCTCT CTCTTGGCCT CCTTTCTAGG TCGGCTGAT TGCTCTTGAA GCTCTCTAGG     2760
GGGGCTCACA CCATAGGCAG ATAACGGTTC CCCACCGGCT CACCTCGTAA GCGCACAAGG    2820
ACTGCTCCCA AAGATCGCCT AGCTGATCTT ATGGAGGTTG CTCGCATGAT CCTTTTTGAT    2880
AATCTCATGA CCAAAATCCC TTAACGTGAG TTTTCGTTCC ACTGAGCGTC AGACCCCGTA    2940
GAAAAGATCC CCGGGTACC                                                2959
```

( 2 ) INFORMATION FOR SEQ ID NO:2:

( i ) SEQUENCE CHARACTERISTICS:
        ( A ) LENGTH: 2959 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Corynebacterium glutamicum
        ( B ) STRAIN: ATCC 13058

( x i ) SEQUENCE DESCRIPTION: SEQ ID NO:2:

```
GGATCCGGTG TATGCCGCAG CAGGCATGAG CAGCCCGAAT ATGCGCCTGC TGGCTGCAAC    60
```

-continued

| | | | | | |
|---|---|---|---|---|---|
| GACCGAGGAA | ATGACCCGCG | TTTTCGGCGC | TGACCAGGCT | TTTTCACATA | GGCTGAGCCG | 120 |
| GTGGCCACTG | CACGTCTCCG | ACGATCCAC | CGCGTACCGC | TGGCATGCCC | AGCACAATCG | 180 |
| CGTGGATCGC | CTAGCTGATC | CCGAAAAAGT | TTTTGCCTTT | TGTAAAAAAC | TTCTCGGTCG | 240 |
| CCCCGCAAAT | TTTCGATTCC | AGATTTTTTA | AAAACCAAGC | CAGAAATACG | ACACACCGTT | 300 |
| TGCAGATAAT | CTGTCTTTCG | GAAAAATCAA | GTGCGATACA | AAATTTTTAG | CACCCCTGAC | 360 |
| GTGCGCAAAG | TCCCGCTTCG | TGAAAATTTT | CGTGCCGCGT | GATTTTCCGC | CAAAAACTTT | 420 |
| AACGAACGTT | CGTTATAATG | GTGTCATGAC | CTTCACGACG | AAGTACCAAA | ATTGGCCCGA | 480 |
| ATCATCAGCT | ATGGATCTCT | CTGATGTCGC | GCTGGAGTCC | GACGCGCTCG | ATGCTGCCGT | 540 |
| CGATTTAAAA | ACGGTGATCG | GATTTTTCCG | AGCTCTCGAT | ACGACGGACG | CGCCAGCATC | 600 |
| ACGAGACTGG | GCCAGTGCCG | CGAGCGACCT | AGAAACTCTC | GTGGCGGATC | TTGAGGAGCT | 660 |
| GGCTGACGAG | CTGCGTGCTC | GGTAGCGCCA | GGAGGACGCA | CAGTAGTGGA | GGATCGAATC | 720 |
| AGTTGCGCCT | ACTGCGGTGG | CCTGATTCCT | CCCCGGCCTG | ACCCGCGAGG | ACGGCGCGCA | 780 |
| AAATATTGCT | CAGATGCGTG | TCGTGCCGCA | GCCAGCCGCG | AGCGCGCCAA | CAAACGCCAC | 840 |
| GCCGAGGAGC | TGGAGGCGGC | TAGGTCGCAA | ATGGCGCTGG | AAGTGCGTCC | CCCGAGCGAA | 900 |
| ATTTTGGCCA | TGGTCGTCAC | AGAGCTGGAA | GCGGCAGCGA | GAATTATCCG | CGATCGTGGC | 960 |
| GCGGTGCCCG | CAGGCATGAC | AAACATCGTA | AATGCCGCGT | TCGTGTGGC | CGTGGCCGCC | 1020 |
| CAGGACGTGT | CAGCGCCGCC | ACCACCTGCA | CCGAATCGGC | AGCAGCGTCG | CGCGTCGAAA | 1080 |
| AAGCGCACAG | GCGGCAAGAA | GCGATAAGCT | GCACGAATAC | CTGAAAAATG | TTGAACGCCC | 1140 |
| CGTGAGCGGT | AACTCACAGG | GCGTCGGCTA | ATCCCAGTC | CAAACCTGGG | AGAAAGCGCT | 1200 |
| CAAAAATGAC | TCTAGCGGAT | TCACGAGACA | TTGACACACC | GGCCTGGAAA | TTTTCCGCTG | 1260 |
| ATCTGTTCGA | CACCCATCCC | GAGCTCGCGC | TGCGATCACG | TGGCTGGACG | AGCGAAGACC | 1320 |
| GCCGCGAATT | CCTCGCTCAC | CTGGGCAGAG | AAAATTTCCA | GGGCAGCAAG | ACCCGCGACT | 1380 |
| TCGCCAGCGC | TTGGATCAAA | GACCCGGACA | CGGGAGAAAC | ACAGCCGAAG | TTATACCGAG | 1440 |
| TTGGTTCAAA | ATCGCTTGCC | CGGTGCCAGT | ATGTTGCTCT | GACGCACGCG | CAGCACGCAG | 1500 |
| CCGTGCTTGT | CCTGGACATT | GATGTGCCGA | GCCACCAGGC | CGGCGGGAAA | ATCGAGCACG | 1560 |
| TAAACCCCGA | GGTCTACGCG | ATTTTGGAGC | GCTGGGCACG | CCTGGAAAAA | GCGTCAGCTT | 1620 |
| GGATCGGCGT | GAATCCACTG | AGCGGGAAAT | GCCAGCTCAT | CTGGCTCATT | GATCCGGTGT | 1680 |
| ATGCCGCAGC | AGGCATGAGC | AGCCCGAATA | TGCGCCTGCT | GGCTGCAACG | ACCGAGGAAA | 1740 |
| TGACCCGCGT | TTTCGGCGCT | GACCAGGCTT | TTCACATAG | GCTGAGCCGG | TGGCCACTGC | 1800 |
| ACGTCTCCGA | CGATCCCACC | GCGTACCGCT | GGCATGCCCA | GCACAATCGC | GTGGATCGCC | 1860 |
| TAGCTGATCT | TATGGAGGTT | GCTCGCATGA | TCTCAGGCAC | AGAAAAACCT | AAAAAACGCT | 1920 |
| ATGAGCAGGA | GTTTTCTAGC | GGACGGGCAC | GTATCGAAGC | GGCAAGAAAA | GCCACTGCGG | 1980 |
| AAGCAAAAGC | ACTTGCCACG | CTTGAAGCAA | GCCTGCCGAG | CGCCGCTGAA | GCGTCTGGAG | 2040 |
| AGCTGATCGA | CGGCGTCCGT | GTCCTCTGGA | CTGCTCCAGG | GCGTGCCGCC | CGTGATGAGA | 2100 |
| CGGCTTTTCG | CCACGCTTTG | ACTGTGGGAT | ACCAGTTAAA | AGCGGCTGGT | GAGCGCCTAA | 2160 |
| AAGACACCAA | GATCATCGAC | GCCTACGAGC | GTGCCTACAC | CGTCGCTCAG | GCGGTCGGAG | 2220 |
| CAGACGGCCG | TGAGCCTGAT | CTGCCGCCGA | TGCGTGACCG | CCAGACGATG | GCGCGACGTG | 2280 |
| TGCGCGGCTA | CGTCGCTAAA | GGCCAGCCAG | TCGTCCCTGC | TCGTCAGACA | GAGACGCAGA | 2340 |
| GCAGCCGAGG | GCGAAAAGCT | CTGGCCACTA | TGGGAAGACG | TGGCGGTAAA | AAGGCCGCAG | 2400 |
| AACGCTGGAA | AGACCCAAAC | AGTGAGTACG | CCCGAGCACA | GCGAGAAAAA | CTAGCTAAGT | 2460 |

| | | | | | |
|---|---|---|---|---|---|
|CCAGTCAACG|ACAAGCTAGG|AAAGCTAAAG|GAAATCGCTT|GACCATTGCA|GGTTGGTTTA|2520|
|TGACTGTTGA|GGGAGAGACT|GGCTCGTGGC|CGACAATCAA|TGAAGCTATG|TCTGAATTTA|2580|
|GCGTGTCACG|TCAGACCGTG|AATAGAGCAC|TTAAGTCTGC|GGGCATTGAA|CTTCCACGAG|2640|
|GACGCCGTAA|AGCTTCCCAG|TAAATGTGCC|ATCTCGTAGG|CAGAAACGG|TTCCCCCGT|2700|
|AGGGGTCTCT|CTCTTGGCCT|CCTTTCTAGG|TCGGGCTGAT|TGCTCTTGAA|GCTCTCTAGG|2760|
|GGGGCTCACA|CCATAGGCAG|ATAACGGTTC|CCCACCGGCT|CACCTCGTAA|GCGCACAAGG|2820|
|ACTGCTCCCA|AAGATCGCCT|AGCTGATCTT|ATGGAGGTTG|CTCGCATGAT|CCTTTTTGAT|2880|
|AATCTCATGA|CCAAAATCCC|TTAACGTGAG|TTTTCGTTCC|ACTGAGCGTC|AGACCCCGTA|2940|
|GAAAAGATCC|CCGGGTACC| | | | |2959|

( 2 ) INFORMATION FOR SEQ ID NO:3:

( i ) SEQUENCE CHARACTERISTICS:
( A ) LENGTH: 2959 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Corynebacterium glutamicum
( B ) STRAIN: ATCC 13058

( x i ) SEQUENCE DESCRIPTION: SEQ ID NO:3:

| | | | | | |
|---|---|---|---|---|---|
|GGATCCGGTG|TATGCCGCAG|CAGGCATGAG|CAGCCCGAAT|ATGCGCCTGC|TGGCTGCAAC|60|
|GACCGAGGAA|ATGACCCGCG|TTTTCGGCGC|TGACCAGGCT|TTTTCACATA|GGCTGAGCCG|120|
|GTGGCCACTG|CACGTCTCCG|ACGATCCCAC|CGCGTACCGC|TGGCATGCCC|AGCACAATCG|180|
|CGTGGATCGC|CTAGCTGATC|CCGAAAAAGT|TTTTGCCTTT|TGTAAAAAAC|TTCTCGGTCG|240|
|CCCCGCAAAT|TTTCGATTCC|AGATTTTTTA|AAACCAAGC|CAGAAATACG|ACACACCGTT|300|
|TGCAGATAAT|CTGTCTTTCG|GAAAAATCAA|GTGCGATACA|AAATTTTTAG|CACCCCTGAC|360|
|GTGCGCAAAG|TCCCGCTTCG|TGAAAATTTT|CGTGCCGCGT|GATTTTCCGC|CAAAAACTTT|420|
|AACGAACGTT|CGTTATAATG|GTGTCATGAC|CTTCACGACG|AAGTACCAAA|ATTGGCCCGA|480|
|ATCATCAGCT|ATGGATCTCT|CTGATGTCGC|GCTGGAGTCC|GACGCGCTCG|ATGCTGCCGT|540|
|CGATTTAAAA|ACGGTGATCG|GATTTTTCCG|AGCTCTCGAT|ACGACGGACG|CGCCAGCATC|600|
|ACGAGACTGG|GCCAGTGCCG|CGAGCGACCT|AGAAACTCTC|GTGGCGGATC|TTGAGGAGCT|660|
|GGCTGACGAG|CTGCGTGCTC|GGCAGCGCCA|GGAGGACGCA|CAGTAGTGGA|GGATCGAATC|720|
|AGTTGCGCCT|ACTGCGGTGG|CCTGATTCCT|CCCCGACCTG|ACCCGCGAGG|ACGGCGCGCA|780|
|AAATATTGCT|CAGATGCGTG|TCGTGCCGCA|GCCAGCCGCG|AGCGCGCCAA|CAAACGCCAC|840|
|GCCGAGGAGC|TGGAGGCGGC|TAGGTCGCAA|ATGGCGCTGG|AAGTGCGTCC|CCCGAGCGAA|900|
|ATTTTGGCCA|TGGTCGTCAC|AGAGCTGGAA|GCGGCAGCGA|GAATTATCCG|CGATCGTGGC|960|
|GCGGTGCCCG|CAGGCATGAC|AAACATCGTA|AATGCCGCGT|TTCGTGTGGC|CGTGGCCGCC|1020|
|CAGGACGTGT|CAGCGCCGCC|ACCACCTGCA|CCGAATCGGC|AGCAGCGTCG|CGCGTCGAAA|1080|
|AAGCGCACAG|GCGGCAAGAA|GCGATAAGCT|GCACGAATAC|CTGAAAAATG|TTGAACGCCC|1140|
|CGTGAGCGGT|AACTCACAGG|GCGTCGGCTA|ACCCCAGTC|CAAACCTGGG|AGAAAGCGCT|1200|
|CAAAAATGAC|TCTAGCGGAT|TCACGAGACA|TTGACACACC|GGCCTGGAAA|TTTTCCGCTG|1260|
|ATCTGTTCGA|CACCCATCCC|GAGCTCGCGC|TGCGATCACG|TGGCTGGACG|AGCAAGACC|1320|
|GCCGCGAATT|CCTCGCTCAC|CTGGGCAGAG|AAAATTTCCA|GGGCAGCAAG|ACCCGCGACT|1380|

```
TCGCCAGCGC TTGGATCAAA GACCCGGACA CGGGAGAAAC ACAGCCGAAG TTATACCGAG    1440

TTGGTTCAAA ATCGCTTGCC CGGTGCCAGT ATGTTGCTCT GACGCACGCG CAGCACGCAG    1500

CCGTGCTTGT CCTGGACATT GATGTGCCGA GCCACCAGGC CGGCGGGAAA ATCGAGCACA    1560

TAAACCCCGA GGTCTACGCG ATTTTGGAGC GCTGGGCACG CCTGGAAAAA GCGCCAGCTT    1620

GGATCGGCGT GAATCCACTG AGCGGGAAAT GCCAGCTCAT CTGGCTTATT GATTCGGTGT    1680

ATGTCGCAGC AGGCATGAGC AGCCCGAATA TGCGCCTGCT GGCTGCAACG ACCGAGGAAA    1740

TGACCCGCGT TTTCGGCGCT GACCAGGCTT TTTCACATAG GCTGAGCCGG TGGCCACTGC    1800

ACGTCTCCGA CGATCCCACC GCGTACCGCT GGCATGCCCA GCACAATCGC GTGGATCGCC    1860

TAGCTGATCT TATGGAGGTT GCTCGCATGA TCTCAGGCAC AGAAAAACCT AAAAAACGCT    1920

ATGAGCAGGA GTTTCTAGC GGACGGGCAC GTATCGAAGC GGCAAGAAAA GCCACTGCGG    1980

AAGCAAAAGC ACTTGCCACG CTTGAAGCAA GCCTGCCGAG CGCCGCTGAA GCGTCTGGAG    2040

AGCTGATCGA CGGCGTCCGT GTCCTCTGGA CTGCTCCAGG GCGTGCCGCC CGTGATGAGA    2100

CGGCTTTTCG CCACGCTTTG ACTGTGGGAT ACCAGTTAAA AGCGGCTGGT GAGCGCCTAA    2160

AAGACACCAA GATCATCGAC GCCTACGAGC GTGCCTACAC CGTCGCTCAG GCGGTCGGAG    2220

CAGACGGCCG TGAGCCTGAT CTGCCGCCGA TGCGTGACCG CCAGACGATG GCGCGACGTG    2280

TGCGCGGCTA CGTCGCTAAA GGCCAGCCAG TCGTCCCTGC TCGTCAGACA GAGACGCAGA    2340

GCAGCCGAGG GCGAAAAGCT CTGGCCACTA TGGGAAGACG TGGCGGTAAA AAGGCCGCAG    2400

AACGCTGGAA AGACCCAAAC AGTGAGTACG CCCGAGCACA GCGAGAAAAA CTAGCTAAGT    2460

CCAGTCAACG ACAAGCTAGG AAAGCTAAAG GAAATCGCTT GACCATTGCA GGTTGGTTTA    2520

TGACTGTTGA GGGAGAGACT GGCTCGTGGC CGACAATCAA TGAAGCTATG TCTGAATTTA    2580

GCGTGTCACG TCAGACCGTG AATAGAGCAC TTAAGTCTGC GGGCATTGAA CTTCCACGAG    2640

GACGCCGTAA AGCTTCCCAG TAAATGTGCC ATCTCGTAGG CAGAAAACGG TTCCCCCCGT    2700

AGGGGTCTCT CTCTTGGCCT CCTTTCTAGG TCGGGCTGAT TGCTCTTGAA GCTCTCTAGG    2760

GGGGCTCACA CCATAGGCAG ATAACGGTTC CCCACCGGCT CACCTCGTAA GCGCACAAGG    2820

ACTGCTCCCA AAGATCGCCT AGCTGATCTT ATGGAGGTTG CTCGCATGAT CCTTTTTGAT    2880

AATCTCATGA CCAAAATCCC TTAACGTGAG TTTTCGTTCC ACTGAGCGTC AGACCCCGTA    2940

GAAAAGATCC CCGGGTACC                                                2959
```

( 2 ) INFORMATION FOR SEQ ID NO:4:

( i ) SEQUENCE CHARACTERISTICS:
        ( A ) LENGTH: 2959 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Corynebacterium glutamicum
        ( B ) STRAIN: ATCC 13058

( x i ) SEQUENCE DESCRIPTION: SEQ ID NO:4:

```
GGATCCGGTG TATGCCGCAG CAGGCATGAG CAGCCCGAAT ATGCGCCTGC TGGCTGCAAC      60

GACCGAGGAA ATGACCCGCG TTTTCGGCGC TGACCAGGCT TTTTCACATA GGCTGAGCCG     120

GTGGCCACTG CACGTCTCCG ACGATCCCAC CGCGTACCGC TGGCATGCCC AGCACAATCG     180

CGTGGATCGC CTAGCTGATC CCGAAAAAGT TTTTGCCTTT TGTAAAAAAC TTCTCGGTCG     240
```

```
CCCCGCAAAT TTTCGATTCC AGATTTTTTA AAAACCAAGC CAGAAATACG ACACACCGTT    300
TGCAGATAAT CTGTCTTTCG GAAAAATCAA GTGCGATACA AAATTTTTAG CACCCCTGAC    360
GTGCGCAAAG TCCCGCTTCG TGAAAATTTT CGTGCCGCGT GATTTCCGC  CAAAAACTTT    420
AACGAACGTT CGTTATAATG GTGTCATGAC CTTCACGACG AAGTACCAAA ATTGGCCCGA    480
ATCATCAGCT ATGGATCTCT CTGATGTCGC GCTGGAGTCC GACGCGCTCG ATGCTGCCGT    540
CGATTTAAAA ACGGTGATCG GATTTTCCG  AGCTCTCGAT ACGACGGACG CGCCAGCATC    600
ACGAGACTGG GCCAGTGCCG CGAGCGACCT AGAAACTCTC GTGGCGGATC TTGAGGAGCT    660
GGCTGACGAG CTGCGTGCTC GGCAGCGCCA GGAGGACGCA CAGTAGTGGA GGATCGAATC    720
AGTTGCGCCT ACTGCGGTGG CCTGATTCCT CCCCGGCCTG ACCCGCGAGG ACGGCGCGCA    780
AAATATTGCT CAGATGCGTG TCGTGCCGCA GCCAGCCGCG AGCGCGCCAA CAAACGCCAC    840
GCCGAGGAGC TGGAGGCGGC TAGGTCGCAA ATGGCGCTGG AAGTGCGTCC CCCGAGCGAA    900
ATTTTGGCCA TGGTCGTCAC AGAGCTGGAA GCGGCAGCGA GAATTATCCG CGATCGTGGC    960
GCGGTGCCCG CAGGCATGAC AAACATCGTA ATGCCGCGT  TTCGTGTGGC CGTGGCCGCC   1020
CAGGACGTGT CAGCGCCGCC ACCACCTGCA CCGAATCGGC AGCAGCGTCG CGCGTCGAAA   1080
AAGCGCACAG GCGGCAAGAA GCGATAAGCT GCACGAATAC CTGAAAAATG TTGAACGCCC   1140
CGTGAGCGGT AACTCACAGG GCGTCGGCTA ACCCCAGTC  CAAACCTGGG AGAAAGCGCT   1200
CAAAAATGAC TCTAGCGGAT TCACGAGACA TTGACACACC GGCCTGGAAA TTTTCCGCTG   1260
ATCTGTTCGA CACCCATCCC GAGCTCGCGC TGCGATCACG TGGCTGGACG AGCGAAGACC   1320
GCCGCGAATT CCTCGCTCAC CTGGGCAGAG AAAATTTCCA GGGCAGCAAG ACCCGCGACT   1380
TCGCCAGCGC TTGGATCAAA GACCCGGACA CGGGAGAAAC ACAGCCGAAG TTATACCGAG   1440
TTGGTTCAAA ATCGCTTGCC CGGTGCCAGT ATGTTGCTCT GACGCACGCG CAGCACGCAG   1500
CCGTGCTTGT CCTGGACATT GATGTGCCGA GCCACCAGGC CGGCGGGAAA ATCGAGCACG   1560
TAAACCCCGA GGTCTACGCG ATTTGGAGC  GCTGGGCACG CCTGGAAAAA GCGCCAGCTT   1620
GGATCGGCGT GAATCCACTG AGCGGGAAAT GCCAGCTCAT CTGGCTCATT GATCCGGTGT   1680
ATGCCGCAGC AGGCATGAGC AGCCCGAATA TGCGCCTGCT GGCTGCAACG ACCGAGGAAA   1740
TGACCCGCGT TTTCGGCGCT GACCAGGCTT TTTCACATAG GCTGAGCCGG TGGCCACTGC   1800
ACGTCTCCGA CGATCCCACC GCGTACCGCT GGCATGCCCA GCACAATCGC GTGGATCGCC   1860
TAGCTGATCT TATGGAGGTT GCTCGCATGA TCTCAGGCAC AGAAAAACCT AAAAAACGCT   1920
ATGAGCAGGA GTTTTCTAGC GGACGGGCAC GTATCGAAGC GGCAAGAAAA GCCACTGCGG   1980
AAGCAAAAGC ACTTGCCACG CTTGAAGCAA GCCTGCCGAG CGCCGCTGAA GCGTCTGGAG   2040
AGCTGATCGA CGGCGTCCGT GTCCTCTGGA CTGCTCCAGG GCGTGCCGCC CGTGATGAGA   2100
CGGCTTTTCG CCACGCTTTG ACTGTGGGAT ACCAGTTAAA AGCGGCTGGT GAGCGCCTAA   2160
AAGACACCAA GATCATCGAC GCCTACGAGC GTGCCTACAC CGTCGCTCAG GCGGTCGGAG   2220
CAGACGGCCG TGAGCCTGAT CTGCCGCCGA TGCGTGACCG CCAGACGATG GCGCGACGTG   2280
TGCGCGGCTA CGTCGCTAAA GGCCAGCCAG TCGTCCCTGC TCGTCAGACA GAGACGCAGA   2340
GCAGCCGAGG GCGAAAAGCT CTGGCCACTA TGGAAGACG  TGGCGGTAAA AAGGCCGCAG   2400
AACGCTGGAA AGACCCAAAC AGTGAGTACG CCCGAGCACA GCGAGAAAAA CTAGCTAAGT   2460
CCAGTCAACG ACAAGCTAGG AAAGCTAAAG GAAATCGCTT GACCATTGCA GGTTGGTTTA   2520
TGACTGTTGA GGGAGAGACT GGCTCGTGGC CGACAATCAA TGAAGCTATG TCTGAATTTA   2580
GCGTGTCACG TCAGACCGTG AATAGAGCAC TTAAGTCTGC GGGCATTGAA CTTCCACGAG   2640
```

| | | | | | | |
|---|---|---|---|---|---|---|
| GACGCCGTAA | AGCTTCCCAG | TAAATGTGCC | ATCTCGTAGG | CAGAAAACGG | TTCCCCCCGT | 2700 |
| AGGGGTCTCT | CTCTTGGCCT | CCTTTCTAGG | TCGGGCTGAT | TGCTCTTGAA | GCTCTCTAGG | 2760 |
| GGGGCTCACA | CCATAGGCAG | ATAACGGTTC | CCCACCGGCT | CACCTCGTAA | GCGCACAAGG | 2820 |
| ACTGCTCCCA | AAGATCGCCT | AGCTGATCTT | ATGGAGGTTG | CTCGCATGAT | CCTTTTTGAT | 2880 |
| AATCTCATGA | CCAAAATCCC | TTAACGTGAG | TTTTCGTTCC | ACTGAGCGTC | AGACCCCGTA | 2940 |
| GAAAAGATCC | CCGGGTACC | | | | | 2959 |